United States Patent [19]

Tocker

[11] 4,049,710
[45] Sept. 20, 1977

[54] NOVEL CARBAMIMIDOYL CHLORIDES AND THEIR USE IN THE SYNTHESIS OF HERBICIDAL TRIAZINEDIONES

[75] Inventor: Stanley Tocker, Wilmington, Del.

[73] Assignee: E. I. Du Pont de Nemours and Company, Wilmington, Del.

[21] Appl. No.: 661,004

[22] Filed: Feb. 24, 1976

[51] Int. Cl.$^2$ ............................................. C07C 125/03
[52] U.S. Cl. ........................... 260/544 C; 260/544 K; 544/211; 544/213; 71/93
[58] Field of Search ........................ 260/544 C, 544 K

[56] References Cited

U.S. PATENT DOCUMENTS

| 3,468,923 | 9/1969 | Koenig et al. | 260/544 C |
| 3,535,360 | 10/1970 | Holtschmidt et al. | 260/544 C |
| 3,699,162 | 10/1972 | Hagemann | 260/544 C |
| 3,902,887 | 9/1975 | Lin | 71/93 |

OTHER PUBLICATIONS

Ulrich et al., Angew. Chem. internat. Edit., vol. 5, No. 8, p. 704–712 (1966).

*Primary Examiner*—Bernard Helfin
*Assistant Examiner*—G. T. Breitenstein

[57] ABSTRACT

Carbamimidoyl chlorides of the formula:

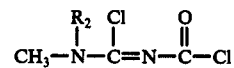

where $R_2$ is alkyl of 1-4 carbon atoms are useful as intermediates in the synthesis of herbicidal triazinediones of the formula:

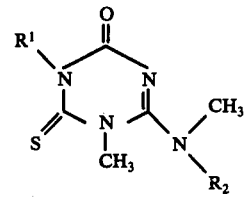

where $R_1$ is certain organic radicals.

2 Claims, No Drawings

NOVEL CARBAMIMIDOYL CHLORIDES AND THEIR USE IN THE SYNTHESIS OF HERBICIDAL TRIAZINEDIONES

BACKGROUND OF THE INVENTION

U.S. Pat. No. 3,902,887 to Lin discloses a class of herbicidal-s-triazines of the general formula:

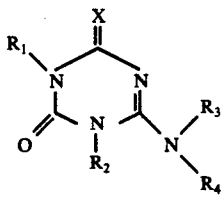

where
X is oxygen or sulfur;
$R_1$ is certain organic radicals including certain acyclic and cyclic radicals;
$R_2$ is hydrogen, lower alkyl, or certain cations;
$R_3$ is hydrogen or certain lower alkyls; and
$R_4$ is certain organic radicals; and various methods for synthesizing these compounds.

Copending U.S. Pat. application No. 621,401, filed Oct. 10, 1975 by Adams et al., discloses and claims certain herbicidal 2-thiotriazinediones of the formula:

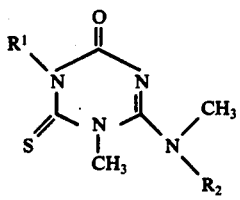

wherein
$R_1$ is certain organic radicals, including certain aliphatic, alicyclic and aromatic radicals, and
$R_2$ is alkyl of 1–4 carbon atoms.

In addition, U.S. Ser. No. 621,401, discloses two processes for preparing those 2-thio compounds, one of which involves the reaction of phosgene with a cyanimide, followed by reaction with a substituted thiourea, which process is, in part, the subject of the present application.

SUMMARY OF THE INVENTION

This invention relates to novel compounds of the following formula:

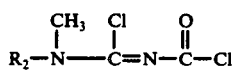

and their use in the synthesis of herbicidal 2-thio-triazinediones of the formula:

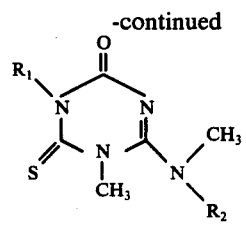

where
$R_1$ is alkyl of 3–6 carbons; cycloalkyl of 5–8 carbons: cycloalkyl of 5–8 carbons substituted with 1 methyl group: cyclohexyl substituted with 1 trifluoromethyl group, or with 2–4 methyl groups; cyclohexenyl; decahydronaphth-1-yl; 3-trifluoromethylphenyl; or

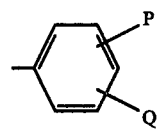

where
P is hydrogen, methyl, chlorine or fluorine; and
Q is hydrogen or chlorine; and
$R_2$ is alkyl of 1–4 carbons.

As indicated in U.S. Ser. No. 621,401, mentioned above, certain of these triazinediones are preferred for their high level of herbicidal activity and include those compounds of formula II where $R_2$ is methyl, and compounds of formula II where $R_1$ is cyclopentyl optionally substituted with one methyl group or where $R_1$ is cyclohexyl optionally substituted with one trifluoromethyl group or one or two methyl groups.

Specifically preferred for its herbicidal activity is the compound 3-cyclohexyl-6-dimethylamino-1-methyl-2-thio-s-triazine-2,4(1H,3H)-dione.

DETAILED DESCRIPTION OF THE INVENTION

Synthesis of the novel intermediate compounds

The compounds of formula I can be prepared by the reaction of an appropriate cyanamide with phosgene in accordance with the following formula:

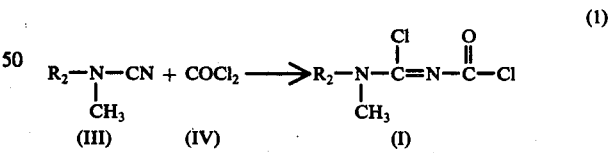

The reaction of the cyanamide and phosgene is carried out at a temperature between 0°–100° C with a preferred temperature of 10°–30° C for purity of product and 30°–70° C for economical operation. Suitable solvents for the reaction are aromatic solvents such as toluene or benzene and other inert organic solvents; alternatively, the reaction can be carried out without solvent in excess phosgene. The mole ratio of phosgene to cyanamide can be from 2:1 to where the phosgene is in large excess, preferably 2:1 to 100:1, with 2:1 to 4:1 being most preferred. Pressure can be from one to 10 atmospheres.

As can be seen, there are several interdependent parameters. In addition, the process can be run continuously or batch. In general, it is preferred to run the process continuously. Also, non-polar solvents or less-polar solvents, such as benzene or toluene, are preferred over more-polar solvents, such as chloroform or methylene chloride. By-product impurities tend to precipitate out of solution in the non-polar solvents and can be removed readily by filtration. In fact, as the solvents become still more polar, they tend to keep all by-products in solution, and become more reactive, thereby failing to satisfy the above-mentioned criterion of being inert with respect to the reactants.

As indicated, the above-mentioned parameters are interdependent. Naturally, one can obtain an excellent yield of the desired product by choosing the most preferred values for each of the various operating parameters, for example, by choosing a preferred solvent, operating at preferred temperature, and with a preferred ratio of reactants. However, it should be understood that good yields can still be obtained even though not all of the parameters are selected as preferred. For example, one can operate the process of the present invention successfully using an inert polar solvent, such as chloroform, by also using a 4.0 molar excess of phosgene in a batch operation. It should also be understood, however, that if one uses a chloroform solvent and lowers the phosgene-cyanamide ratio too far, such as to 1:1, essentially all by-products are obtained.

SYNTHESIS OF THE FINAL PRODUCT TRIAZINEDIONES

The compounds of formula II can be prepared by reacting a 1-substituted-3-methylthiourea with the N-alkyl-N-methyl-N'-chlorocarbonylcarbamimidoyl chloride of formula I in accordance with the following equation:

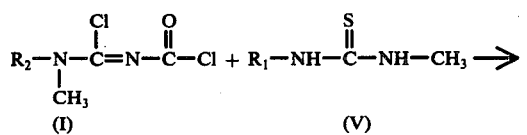

(2)

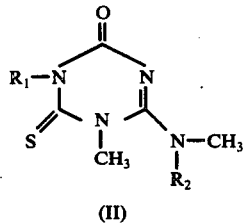

The thioureas utilized are commercially available or may be prepared from the appropriate amine and methyl isothiocyanate. The reaction of the carbamimidoyl chlorides and thioureas is carried out in the presence of an acid acceptor at a temperature between 0°–100° C with a preferred temperature of 0°–30° C for purity of product and 30°–70° C for economical operation. Suitable solvents for the operation are halogen-substituted aliphatics, ethers, halogen- and alkyl-substituted aromatics or other inert organic solvents. The ratio of carbamimidoyl chloride to thioureas is from 0.9 to 1.1.

EXAMPLE 1

N,N-Dimethyl-N'-chlorocarbonylcarbamimidoyl Chloride

In a flask equipped with an acetone-dry ice condenser, drying tube, mechanical stirrer and addition funnel, a mixture of 59.0 grams (0.60 mole) phosgene, 250 ml. anhydrous toluene and 20.0 grams anhydrous sodium carbonate powder is prepared. The purpose of the sodium carbonate is to remove traces of hydrogen chloride. The mixture is stirred for 0.5 hour and then treated dropwise with stirring over a 20 minute period at room temperature with a solution of 20.0 grams (0.29 mole) of dimethyl cyanamide in 50 ml anhydrous toluene. The mixture is then stirred for 17 hours, and then filtered under rigorously anhydrous conditions. Excess phosgene and toluene are removed under vacuum at 60° C., leaving 40.1 grams (83%) of N,N-dimethyl-N'-chlorocarbonylcarbamimidoyl chloride as a pale-yellow, moisture-sensitive oil, B.P. 114°–115° C at 1.5 mm Hg. This material is of sufficient purity for use as an intermediate. This material can be further vacuum distilled but with some accompanying decomposition. A nuclear magnetic resonance peak at 3.25 δ(CDCl₃) characteristic of the nitrogen-methyl group was observed. An infrared peak at 1750 cm⁻¹ showed the presence of the chlorocarbonyl group.

Using the appropriate N-alkyl-N-methyl cyanamide in place of dimethyl cyanamide as in Example 1, the following carbamimidoyl chlorides of formula I can be prepared:

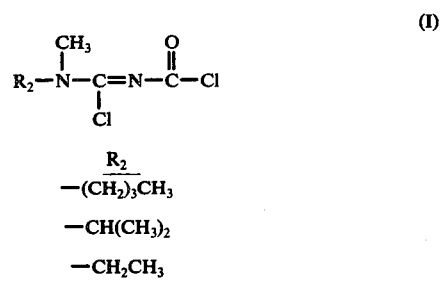

EXAMPLE 2

3-Cyclohexyl-1-methyl-6-dimethylamino-2-thio-s-triazine-2.4(1H.3H)-dione

A solution of 59.0 grams (0.349 mole) of N,N-dimethyl-N'-chlorocarbonylcarbamimidoyl chloride in 612 ml of tetrahydrofuran is used to treat, dropwise over a 70 minute period at −5° C., a mixture of 60.0 grams (0.349 mole) 1-cyclohexyl-3-methylthiourea and 91.0 grams (0.9 mole) triethylamine in 1346 ml tetrahydrofuran. The resulting mixture is stirred for 17 hours, filtered and the insoluble amine salt is washed with tetrahydrofuran. The solvent is stripped from the combined filtrate and tetrahydrofuran wash and the residue is washed successively with ether and water. Drying in a vacuum oven gives 82 grams, 88%, of 3-cyclohexyl-1-methyl-6-dimethylamino-2-thio-s-triazine-2,4(1H,3H)-dione, m.p. 209° C.

With the appropriate N-alkyl-N-methyl cyanamide and 1-substituted-3-methylthiourea, the above procedure was used to make the following 2-thiotriazinediones of formula II.

| Example | R₁ | R₂ | Melting Point, ° C. |
|---|---|---|---|
| 2 a | t-butyl | methyl | 155 – 156 |
| b | isopropyl | methyl | 145 – 146 |
| c | 4-chlorophenyl | methyl | 240 – 241.5 |
| d | cyclohexyl | butyl | 104 – 105 |

Similarly, other analogs can be prepared as shown below:

| Example | R₁ | R₂ |
|---|---|---|
| 2 e | n-propyl | methyl |
| f | n-hexyl | methyl |
| g | neopentyl | methyl |
| h | 1-ethylpropyl | methyl |
| i | cyclopentyl | methyl |
| j | cyclooctyl | methyl |
| k | 3-methylcyclopentyl | methyl |
| l | 3-methylcyclohexyl | methyl |
| m | 3,5-dimethylcyclohexyl | methyl |
| n | 2-cyclohexen-1-yl | methyl |
| o | decahydronapth-1-yl | methyl |
| p | phenyl | methyl |
| q | 3-trifluoromethylphenyl | methyl |
| r | 2-fluorophenyl | methyl |
| s | 3,4-dichlorophenyl | methyl |
| t | cyclohexyl | ethyl |
| u | 2-methylcyclooctyl | methyl |
| v | 3-trifluoromethylcyclohexyl | methyl |
| w | 3,3,5,5-tetramethylcyclohexyl | methyl |
| x | 3-methylphenyl | methyl |
| y | 4-chloro-2-fluorophenyl | methyl |

FORMULATION OF THE COMPOUNDS

Useful formulations of the compounds of formula II can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 1% to 99% by weight of active ingredient(s) and at least one of a) about 0.1% to 20% surfactants(s) and b) about 5% to 99% solid or liquid diluent(s). More specifically, they will contain these ingredients in the following approximate proportions:

| | Percent by weight | | |
|---|---|---|---|
| | Active Ingredient | Diluent(s) | Surfactant(s) |
| Wettable Powders | 20 – 90 | 0 – 74 | 1 – 10 |
| Oil Suspensions, Emulsions, Solutions (including Emulsifiable Concentrates) | 5 – 50 | 40 – 95 | 0 – 15 |
| Aqueous Suspensions | 10 – 50 | 40 – 84 | 1 – 20 |
| Dusts | 1 – 25 | 70 – 99 | 0 – 5 |
| Granules and Pellets | 1 – 95 | 5 – 99 | 0 – 15 |
| High Strength Compositions | 90 – 99 | 0 – 10 | 0 – 2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers," 2nd, Edn., Dorland Books, Caldwell, N.J. The more absorptive diluents are preferred for wettable powders and the denser ones for dusts. Typical liquid diluents and solvents are described in Marsden, "Solvents Guide," 2nd, Edn., Interscience, New York, 1950. Solubility under 0.1% is preferred for suspension concentrates; solution concentrates are preferably stable against phase separation at 0° C. "McCutcheon's Detergents and Emulsifiers Annual," Allured Publ. Corp., Ridgewood, New Jersey, as well as Sisely and Wood, "Encyclopedia of Surface Active Agents," Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration," *Chemical Engineering*, Dec. 4, 1967, pp. 147ff. and "Perry's Chemical Engineer's Handbook," 4th Edn., McGraw-Hill, N.Y., 1963, pp. 8–59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, March 14, 1967, Col. 5 Line 43 through Col. 7 Line 62 and Ex. 8, 12, 15, 39, 41, 52, 53, 58, 132, 138–140, 162–164, 166, 167, 169–182.

H. Gysin and E. Knusli, U.S. Pat. No. 2,891,855, June 23, 1959, Col. 3 Line 66 through Col. 5 Line 17 and Examples 1–4.

G. C. Klingman, "Weed Control as a Science," John Wiley & Sons, Inc., New York, 1961 pp. 81–96.

J. D. Fryer and S. A. Evans, "Weed Control Handbook," 5th Edn. Blackwell Scientific Publications, Oxford, 1968, pp. 101–103.

EXAMPLE 3

| Wettable Powder | |
|---|---|
| 3-cyclohexyl-1-methyl-6-dimethylamino-2-thio-s-triazine-2,4(1H,3H)-dione | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S.N. 50 sieve (0.3 mm opening) before packaging.

All compounds of the invention may be formulated in the same manner.

EXAMPLE 4

| Extruded Pellet | |
|---|---|
| 3-isopropyl-1-methyl-6-dimethylamino-2-thio-s-triazine-2,4(1H,3H)-dione | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass a U.S. Ser. No. 20 sieve (0.84 mm openings). The granules held on a U.S. Ser. No. 40 sieve (0.42 mm openings) may be packaged for use and the fines recycled.

EXAMPLE 5

| Aqueous Suspension | |
|---|---|
| 3-p-chlorophenyl-1-methyl-6-dimethylamino-2-thio-s-triazine-2,4(1H,3H)-dione | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns.

EXAMPLE 6

| 3-cyclohexyl-1-methyl-6-dimethyl amino-2-thio-s-triazine-2,4(1H,3H)-dione | 20% |
|---|---|
| isophorone | 67% |
| dimethylformamide | 5% |
| blend of oil soluble sulfonates and polyethyleneglycol ethers | 8% |

The above ingredients are blended with warming to produce a homegenous emulsifiable concentrate.

EXAMPLE 7

| Wettable Powder | |
|---|---|
| 3-cyclohexyl-1-methyl-6-dimethylamino-2-thio-s-triazine-2,4(1H,3H)-dione | 80% |
| dodecylphenyl polyethylene glycol ether | 2% |
| sodium ligninsulfonate | 4% |
| sodium silicoaluminate | 6% |
| kaolinite | 8% |

The ingredients are thoroughly blended.

The liquid surfactant is added by spraying upon the solid ingredients in the blender. After grinding in a hammer mill to produce particles essentially all below 100 microns, the material is reblended and sifted through a U.S. Ser. No. 50 seive (0.3 mm opening) and packaged.

EXAMPLE 8

| Granule | |
|---|---|
| wettable powder of Example 7 | 10% |
| attapulgite granules (U.S.S.N. 20 – 40; 0.84 – 0.42 mm) | 90% |

A slurry of wettable powder containing 50% solids is sprayed on the surface of attapulgite granules in a double-cone blender. The granules are dried and packaged.

EXAMPLE 9

| High Strength Concentrate | |
|---|---|
| 3-(3,4-dichlorophenyl)-1-methyl-6-dimethylamino-2-thio-s-triazine-2,4- | 99% |

| -continued | |
|---|---|
| High Strength Concentrate | |
| (1H,3H)-dione | |
| trimethylnonyl polyethylene glycol ether | 1% |

The surfactant is sprayed upon the active ingredient in a blender and the mixture sifted through a U.S. Ser. No. 40 sieve (0.42 mm openings) prior to packaging. The concentrate may be formulated further for practical use.

EXAMPLE 10

| Dust | |
|---|---|
| high strength concentrate, Example 9 | 25.4% |
| pyrophyllite, powdered | 74.6% |

The ingredients are thoroughly blended and packaged for use.

USE OF THE COMPOUNDS

The compounds of formula II are useful for the control of undesired vegetation. They can be used wherever weed control is required, such as on industrial sites, railroad rights-of-way, and locations adjacent to crop lands.

The precise amount of the compounds of formula II to be used in any given situation will vary according to the particular end result desired, the use involved, the plant and soil involved, the formulation used, the mode of application, prevailing weather conditions, foliage density, and like factors. Since so many variables play a role, it is not possible to state a rate of application suitable for all situations. Broadly speaking, the compounds of the invention are used at levels of about 1 to about 25 kilograms per hectare. The lower rates in this range will generally be selected on lighter soils, soils low in organic matter content, or in situations where maximum persistence is not necessary.

The compounds of formula II can be combined with any other herbicide and they are particularly useful in combination with herbicides of the substituted urea, uracil, or s-triazine types for controlling a broad spectrum of weeds.

The compounds of this invention are especially useful for controlling undesired vegetation due to their low water solubility which results in longer soil residual activity. For example, 3-cyclohexyl-6-dimethylamino-1-methyl-2-thio-s-triazine-2,4(1H,3H)-dione has a water solubility of 2.6 ppm.

EXAMPLE 11

Test Procedure

Seeds of crabgrass (Digitaria spp.), spp.), barnyardgrass (*Echionochloa crusgalli*), wild oats (*Avena fatua*), *Cassia tora*, morningglory (*Ipomoea* spp.), cocklebur (*Xanthium* spp.), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the third trifoliate leaf expanding, crabgrass with two leaves, barnyardgrass with two leaves, wild oats with one leaf, cassia with three leaves (including the cotyledonary ones), moringglory with four leaves (including the cotyledonary ones), cocklebur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for 16 days then all species were compared to controls and visually rated for response to treatment. A quantitative rating for type of injury was also made on a scale of 0 to 10; rating of 10 means complete kill, a rating of 0 means no injury. A qualitative rating for type of injury was also made; the letter C stands for chlorosis/necrosis; B indicates foliar burn; D stands for defoliation; L means lodging; and G represents growth retardation.

PLANT RESPONSE DATA

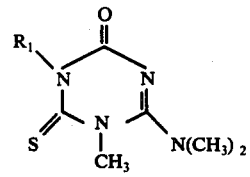

| $R_1=$ | type tested | kg/ha | bush bean | cotton | sorghum | corn | soybean | wheat | wild-oats | rice | barnyard grass | crab-grass | morning-glory | cocklebur | cassia | nutsedge |
|---|---|---|---|---|---|---|---|---|---|---|---|---|---|---|---|---|
| Cyclohexyl | Pre-emergence | 2 | 10C | 10C | 10C | 10C | 10C | 10C | 10C | 10C | 10C | 10C | 10C | 10C | 10C | 9C |
| | Post-emergence | 2 | — | — | 10C | 9C | 9C | 10C | 10C | 8C | 10C | 10C | 10C | 10C | 10C | 7C |
| 4-chlorophenyl | Pre-emergence | 0.4 | 7B | 5B | 1B | 2B | 4B | 1B | 2B | 1B | 8B | 7B | 7B | 4B | 4B | 0 |
| | Post-emergence | 0.4 | — | — | 10C | 9C | 5C | 10C | 10C | 3C | 10C | 10C | 9C | 4C | 10C | 5C |
| isopropyl | Pre-emergence | 0.4 | 7C | 7C 8D | 8C | 6G 5L | 10C | 5C | 7B | 7C | 8C | 8C | 10C | 10C | 10C | 1C |
| | Post-emergence | 0.4 | — | — | 4C | 1C 6G | 9C | 9C | 10C | 5C | 9C | 8C | 10C | 9C | 10C | 5G |

I claim:
1. A compound of the formula:

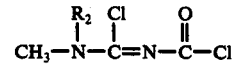

where $R_2$ is alkyl of 1 through 4 carbon atoms.

2. The compound of claim 1 where $R_2$ is methyl, N,N-dimethyl-N'-chlorocarbonylcarbamimidoyl chloride.

* * * * *